(12) United States Patent
Isham

(10) Patent No.: US 9,707,379 B2
(45) Date of Patent: *Jul. 18, 2017

(54) RECTAL BALLOON WITH LOCKING STOPPER

(71) Applicant: RadiaDyne, LLC, Houston, TX (US)

(72) Inventor: John Isham, Houston, TX (US)

(73) Assignee: RadiaDyne LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/061,906

(22) Filed: Mar. 4, 2016

(65) Prior Publication Data

US 2016/0184559 A1    Jun. 30, 2016

Related U.S. Application Data

(63) Continuation-in-part of application No. 14/517,932, filed on Oct. 20, 2014, which is a continuation-in-part
(Continued)

(51) Int. Cl.
*A61M 29/00* (2006.01)
*A61M 25/10* (2013.01)
(Continued)

(52) U.S. Cl.
CPC ........ *A61M 25/10* (2013.01); *A61M 25/1002* (2013.01); *A61N 5/10* (2013.01); *A61N 5/1078* (2013.01); *A61B 2017/00274* (2013.01); *A61B 2017/00557* (2013.01); *A61B 2017/22069* (2013.01); *A61B 2018/00547* (2013.01); *A61M 2025/0008* (2013.01); *A61M 2025/0233* (2013.01); *A61M 2202/02* (2013.01); *A61M 2205/59* (2013.01); *A61M 2210/166* (2013.01); *A61N 5/1071* (2013.01); *A61N 2005/1072* (2013.01); *A61N 2005/1097* (2013.01)

(58) Field of Classification Search
CPC ................. A61M 29/00; A61N 5/1049; A61N 2005/1097; A61B 2018/00547
USPC .... 606/191–199; 604/96.01, 101.05, 103.03, 604/100.01, 100.02, 117, 180, 192; 24/30.5 R, 132 A, 132 AA, 132 WL; 128/DIG. 26
See application file for complete search history.

(56) References Cited

U.S. PATENT DOCUMENTS 3,509,884 A    5/1970 Bell
3,799,170 A    3/1974 Walsh
(Continued)

FOREIGN PATENT DOCUMENTS

WO    9423676    10/1994
WO    2008148150    12/2008

OTHER PUBLICATIONS

Wootton et al., Effectiveness of a novel gas-release endorectal balloon in the removal of rectal gas for prostate proton radiation therapy J. Appl. Clin. Med. Phys. 13(5): 190-197 (2012).
(Continued)

*Primary Examiner* — John Lacyk
(74) *Attorney, Agent, or Firm* — Boulware & Valoir

(57) ABSTRACT

A prostate immobilizing balloon that on full inflation cups the prostate to hold it during treatment is combined with a locking member so that the balloon does not shift during use. Methods of using same are also provided.

20 Claims, 9 Drawing Sheets

Related U.S. Application Data of application No. 14/065,127, filed on Oct. 28, 2013, which is a continuation-in-part of application No. 13/444,626, filed on Apr. 11, 2012, now Pat. No. 8,603,129.

(51) Int. Cl.
*A61N 5/10* (2006.01)
*A61B 18/00* (2006.01)
*A61B 17/00* (2006.01)
*A61B 17/22* (2006.01)
*A61M 25/00* (2006.01)
*A61M 25/02* (2006.01)

(56) References Cited

U.S. PATENT DOCUMENTS

| | | | |
|---|---|---|---|
| 4,043,345 A | 8/1977 | Kramann |
| 4,311,146 A | 1/1982 | Wonder |
| 4,584,730 A | 4/1986 | Rajan |
| 4,650,463 A | 3/1987 | LeVeen |
| 4,784,133 A | 11/1988 | Mackin |
| 4,813,429 A | 3/1989 | Eshel |
| 4,893,367 A | 1/1990 | Heimreid |
| 4,994,033 A | 2/1991 | Shockey |
| 5,116,310 A | 5/1992 | Seder |
| 5,234,454 A | 8/1993 | Bangs |
| 5,355,087 A | 10/1994 | Claiborne |
| 5,360,414 A | 11/1994 | Yarger |
| 5,433,252 A | 7/1995 | Wolf |
| 5,476,095 A | 12/1995 | Schnall |
| 5,512,051 A | 4/1996 | Wang |
| 5,527,280 A | 6/1996 | Goelz |
| 5,545,220 A | 8/1996 | Andrews |
| 5,679,423 A | 10/1997 | Shah |
| 5,704,913 A | 1/1998 | Abele |
| 5,832,550 A | 11/1998 | Hauger |
| 5,833,915 A | 11/1998 | Shah |
| 5,868,776 A | 2/1999 | Wright |
| 5,879,499 A | 3/1999 | Corvi |
| 5,924,456 A | 7/1999 | Simon |
| 5,996,639 A | 12/1999 | Gans |
| 6,022,313 A | 2/2000 | Ginn |
| 6,024,753 A | 2/2000 | Claren |
| 6,102,929 A | 8/2000 | Conway |
| 6,156,053 A | 12/2000 | Gandhi |
| 6,249,708 B1 | 6/2001 | Nelson |
| 6,291,543 B1 | 9/2001 | Shah |
| 6,327,724 B1 | 12/2001 | Sharrock |
| 6,352,077 B1 | 3/2002 | Shah |
| 6,460,541 B1 | 10/2002 | Shah |
| 6,478,789 B1 | 11/2002 | Spehalski |
| 6,520,977 B2 | 2/2003 | Piraka |
| 6,663,646 B1 | 12/2003 | Shah |
| 6,712,832 B2 | 3/2004 | Shah |
| 6,733,512 B2 | 5/2004 | McGhan |
| 6,746,465 B2 | 6/2004 | Diederich |
| 6,805,662 B2 | 10/2004 | Shah |
| 6,827,710 B1 | 12/2004 | Mooney |
| 6,875,193 B1 | 4/2005 | Bonnette |
| 6,963,771 B2 | 11/2005 | Scarantino |
| 6,981,980 B2 | 1/2006 | Sampson |
| 7,112,186 B2 | 9/2006 | Shah |
| 7,216,385 B2 | 5/2007 | Hill |
| 7,220,252 B2 | 5/2007 | Shah |
| 7,361,134 B2 | 4/2008 | Rozenfeld |
| 7,470,251 B2 | 12/2008 | Shah |
| 7,976,497 B2 | 7/2011 | Shah |
| 8,454,648 B1 * | 6/2013 | Isham ............ A61N 5/1049 128/DIG. 26 |
| 8,500,771 B2 | 8/2013 | Isham |
| 2001/0027307 A1 | 10/2001 | Dubrul |
| 2003/0028097 A1 | 2/2003 | D'Amico |
| 2003/0088209 A1 | 5/2003 | Chiu |
| 2005/0004592 A1 | 1/2005 | Criscuolo |
| 2005/0222329 A1 | 10/2005 | Shah |
| 2005/0267509 A1 | 12/2005 | Davis |
| 2006/0094923 A1 | 5/2006 | Mate |
| 2006/0212064 A1 | 9/2006 | Shah |
| 2007/0058778 A1 | 3/2007 | Coleman |
| 2007/0212559 A1 | 9/2007 | Shah |
| 2007/0239110 A1 | 10/2007 | Shah |
| 2007/0299463 A1 | 12/2007 | Shah |
| 2008/0188802 A1 | 8/2008 | Shah |
| 2008/0262449 A1 | 10/2008 | Shah |
| 2008/0262450 A1 | 10/2008 | Shah |
| 2009/0082724 A1 | 3/2009 | Shah |
| 2009/0236510 A1 | 9/2009 | Lacroix |

OTHER PUBLICATIONS

Su, et al., Abstract 3192 Reduction of Prostate Intrafraction Motion using Gas-release Rectal Balloons, I. J. Radiation Oncology*Biology*Physics 81(2) (S. 2011).

Su, et al., Reduction of prostate intrafraction motion using gas-release rectal balloons, 5869 Med. Phys. 39 (10): 5869 (2012).

* cited by examiner

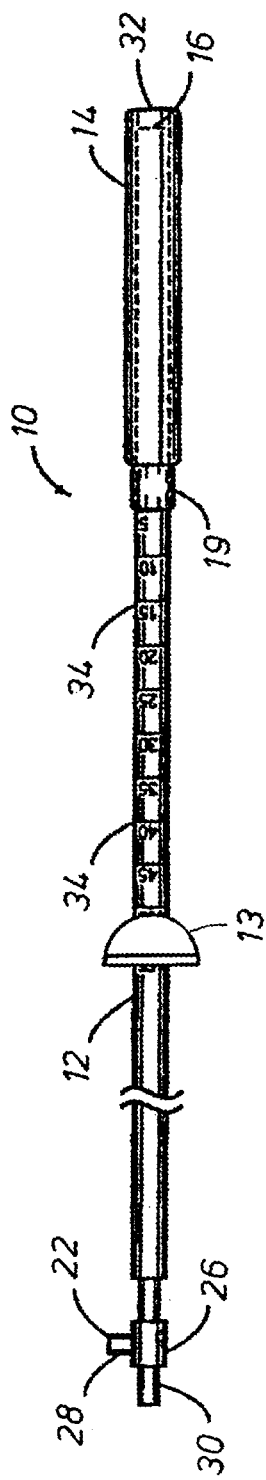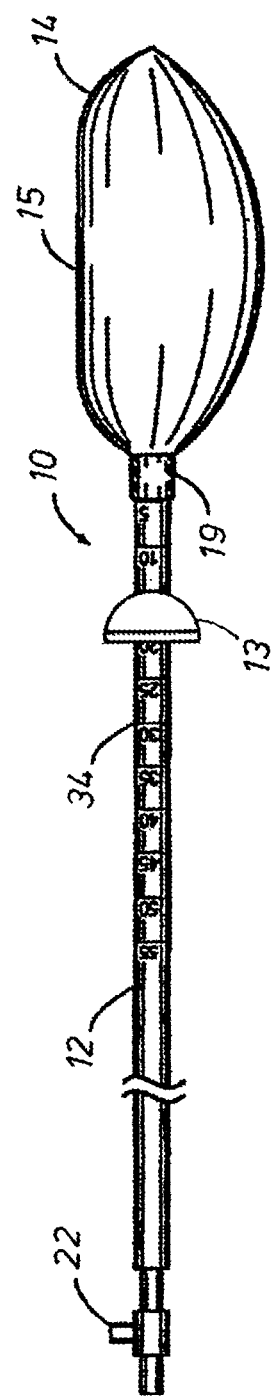

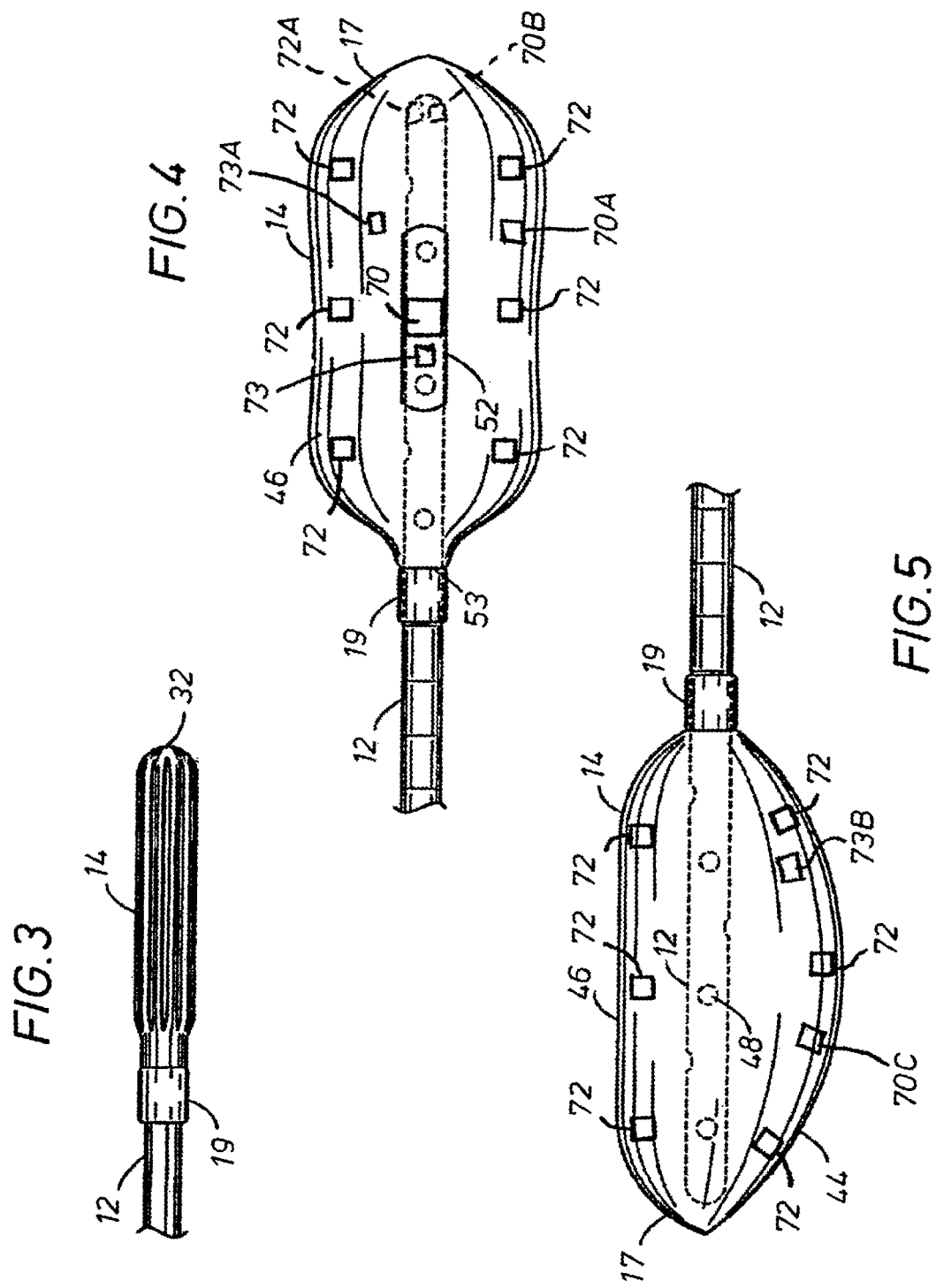

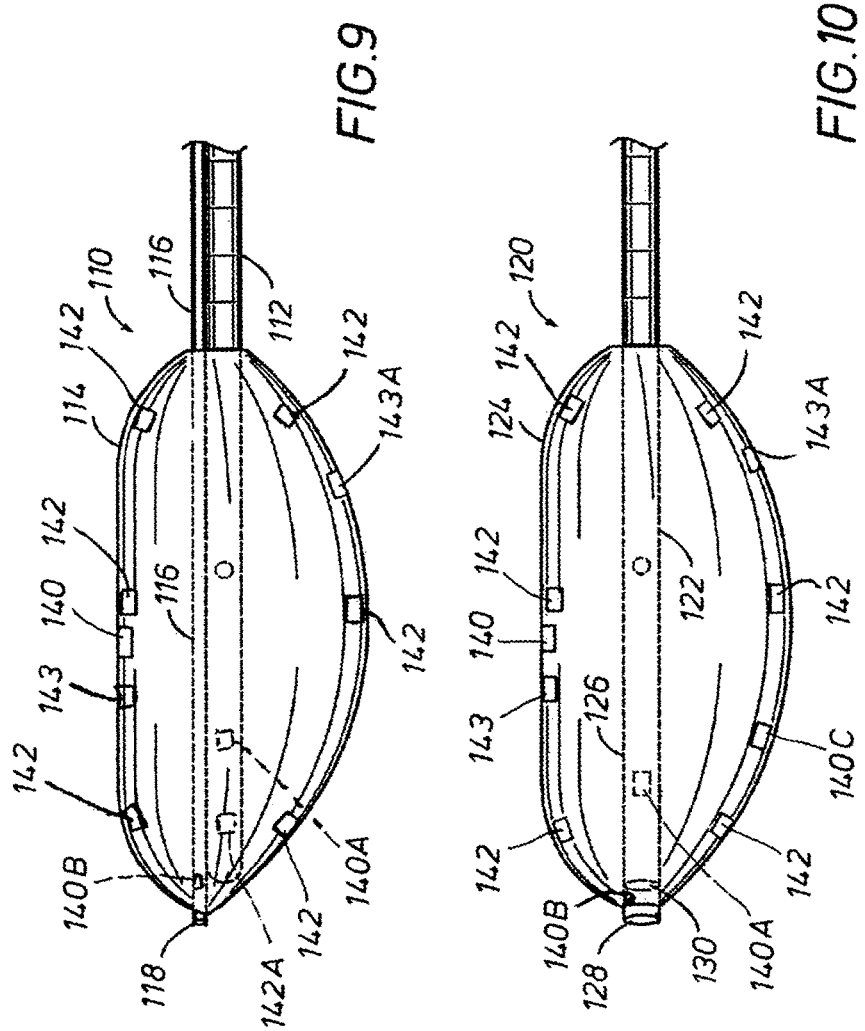

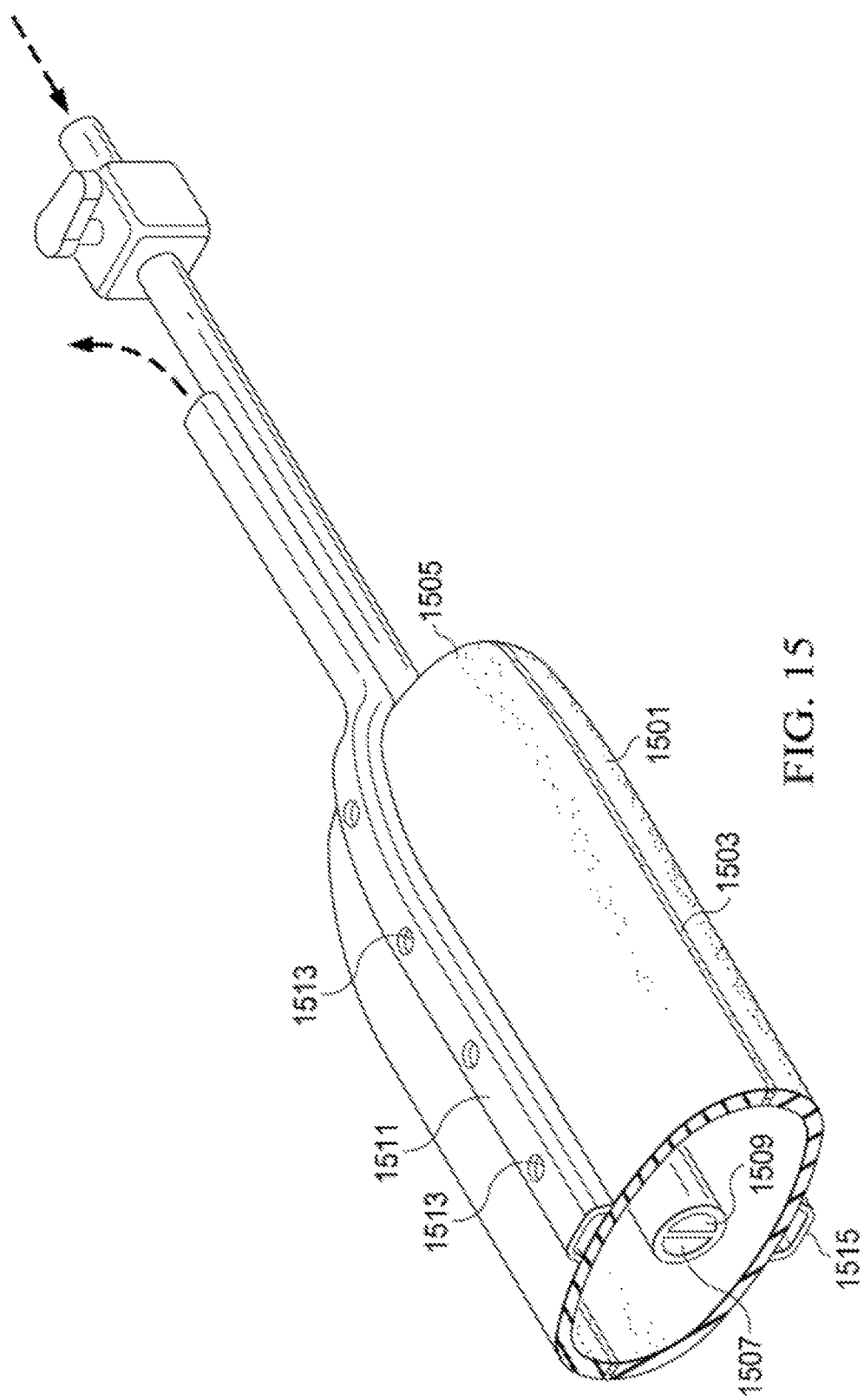

RECTAL BALLOON WITH LOCKING STOPPER

PRIOR RELATED APPLICATIONS

This application is a continuation-in-part of Ser. No. 12/410,639 filed Mar. 25, 2009 (issued as U.S. Pat. No. 8,454,648).

It is also a continuation-in-part of each of the following: Ser. No. 11/623,702 filed on Jan. 16, 2007; Ser. No. 11/933,018 filed on Oct. 31, 2007; Ser. No. 11/966,544 filed on Dec. 28, 2007; Ser. No. 12/034,470 filed on Feb. 20, 2008 (U.S. Pat. No. 8,080,031); Ser. No. 12/141,270 filed on Jun. 18, 2008; Ser. No. 12/410,639 filed on Mar. 25, 2009 (U.S. Pat. No. 8,454,648); Ser. No. 12/412,017 filed on Mar. 26, 2009; Ser. No. 12/748,494, filed on Mar. 29, 2010 (U.S. Pat. No. 8,241,317); Ser. No. 13/444,626 filed Apr. 11, 2012 (U.S. Pat. No. 8,603,129); Ser. No. 14/065,127 filed on Oct. 28, 2013 (pending); Ser. No. 14/198,087 filed on Mar. 5, 2014 (pending); Ser. No. 14/445,946 filed on Jul. 29, 2014 (pending), Ser. No. 14/517,932 filed on Oct. 20, 2014 (pending), and Ser. No. 12/707,389 filed on Feb. 17, 2010 (U.S. Pat. No. 8,500,771). Each of these US Applications is incorporated by reference in its entirety for all purposes.

FIELD OF THE DISCLOSURE

The present disclosure relates to rectal balloons that are used for immobilizing the region surrounding the prostate. In particular, a rectal balloon with locking stopper is provided.

BACKGROUND OF THE DISCLOSURE

Treatment of prostate cancer using radiation therapy is difficult due to the prostate's position near radiation-sensitive tissues, and is further complicated by prostate motion. Adenocarcinoma of the prostate commonly occurs in the posterior portion of the prostate gland, which is in very close proximity to the rectal wall. To date, external beam radiation treatment, urethrograms, CT scans and magnetic resonance imaging (MRI) have all been used to visually localize the prostate, as well as the normal critical structures in the surrounding area.

U.S. Pat. No. 5,476,095 proposes an insertable pickup probe for use in providing diagnostic MRI images. The pickup probe, in its preferred embodiment, is proposed for use in imaging the male prostate and comprises an elongated shaft supporting an inflatable patient interface balloon at its distal end. The interface balloon comprises an inner balloon and an outer balloon, between which a receiving coil is positioned. A lumen for air supply is provided in the shaft for expanding the inner balloon against the outer balloon to place the receiving coil in close proximity to the area of interest in order to provide MRI images.

Typically, the planning of radiation therapy for the treatment of prostate cancer involves the patient undergoing a CT-based simulation scan of the pelvis to determine the location of the prostate gland. In the simulation phase, the patient is placed on CT equipment that is preferably similar to the radiation treatment equipment (except that it does not generate the high energy radiation beam). The simulation equipment is positioned to simulate the delivery of the sequence of treatment beams prescribed by the treating oncologist. Normally, during the simulation procedure, CT images are acquired. These CT images allow the oncologist to locate the position of the tumor and help to facilitate the composition of a radiation treatment plan. This treatment plan delineates the positions of the radiation equipment components for delivery of the treatment beams.

During the actual treatment phase, the patient is placed in the same position on the treatment equipment as in the simulation scans. Radiation-emitting devices are generally known and used for radiation therapy in the treatment of patients. Typically, a radiation therapy device includes a gantry, which can be swiveled around a horizontal axis of rotation in the course of a therapeutic treatment. A linear accelerator is located in the gantry for generating a high-energy radiation beam for therapy. During treatment, the radiation beam is provided by this equipment and is delivered to the patient at the precise location as delineated by the physician during simulation. A further feature of radiation therapy involves portal images, which are commonly used in radiation therapy to verify and record the patient tumor location. Portal images include manual (film) and electronic images (EPI) taken before and/or after the treatment.

During external beam radiation therapy, radiation is directed to the target prostate, which is near the rectal wall. Typically, a plurality of beams are used, and where the beams cross the highest radiation is provided. A misdirected radiation beam may perforate the rectal wall causing radiation proctitis (rectal bleeding). This toxicity is related to the total radiation dose prescribed and the volume of the anterior rectal wall receiving a high radiation dose. A major factor limiting radiation oncologists' attempts to reduce the volume of the anterior rectal wall receiving a high radiation dose is the position of the prostate gland as well as the intrinsic motion up to 5 mm in the anterior to posterior direction caused by rectal peristalsis. Accordingly, oncologists generally will add a margin to the radiation field in order to ensure that the entire prostate gland receives the prescription dose. This margin is typically on the order of 5 to 15 mm. As a consequence, lower doses of radiation may need to be used so as not to overexpose radiation sensitive healthy structures. However, this may lead to inadequate radiation treatment and a higher probability of local cancer recurrence.

US20030028097 proposes an insertable probe for immobilizing a region of interest during staging and radiation therapy thereof. In particular, a balloon is proposed having a rectangular cross section connected to a shaft. The shaft extends to an end of the balloon so as to allow fluid flow through an interior of the shaft and into the balloon so as to selectively inflate the balloon once the balloon is installed into the rectal cavity. The balloon, shaft and handle are bonded together so that they move radially as a single unit when torque is applied. A syringe is provided which connects the shaft and serves as an air pump to deliver a volume-limited amount of air to the air lumen of the shaft to the balloon. A stop cock is provided to maintain the air within the balloon.

One of the problems with the subject of US20030028097 is the discomfort associated with installing the rectal balloon within the rectal cavity. In particular, a relatively sturdy and wide diameter shaft is connected to a relatively large thick-walled balloon. Because the balloon is not supported by anything other than by the shaft, the balloon is formed of a relatively rugged and thick material. Because of the relatively large size of the shaft and the thick material of the rectangular-cross section balloon, the installation of the rectal balloon creates a large amount of discomfort for a patient. In addition, it is often difficult for the medical personnel to know exactly how far within the rectum the balloon has been installed. Thus, it is difficult to achieve a standardized and fixed position of the balloon during each and every use. The medical personnel must generally approximate the desired position of the balloon within the rectal cavity. As such, a need has developed whereby the rectal balloon can be formed of a minimal diameter shaft and of a balloon of relatively thin material.

When the rectal balloon of US20030028097 is in an inflated condition, the outer surface is generally rounded. As such, the prostate will tend to balance on the curved (convex) surface rather than be properly seated thereon. Since seating is important for proper use, this device requires that the physician approximate a seated position rather than providing any feedback of the seated position. When the balloon is in an outwardly curved (convex) inflated condition, the prostate will have a tendency to slide to one side of the balloon or the other. As such, a need developed to provide a rectal balloon that retains the prostate in a proper seated position when the balloon is in a fully inflated condition.

As discussed above, a very important consideration when treating patients using radiation therapy is that the proper dose of radiation reaches the treatment site. This is very important whether the treatment method utilizes implanted radiation seeds or external beams of radiation. Excessive dosing of the patient can lead to severe side effects including impotence and urinary incontinence. In fact, estimates provide that as many as half the patients treated suffer incontinence and/or impotence. A proper treatment plan should deliver an adequate amount of radiation to the treatment site while minimizing the dose delivered to the surrounding tissues, and thus minimizing these side effects.

U.S. Pat. No. 6,963,771 describes a method, system and implantable device for radiation dose verification. The method includes (a) placing at least one wireless implantable sensor in a first subject at a target location; (b) administering a first dose of radiation therapy into the first subject; (c) obtaining radiation data from the at least one wireless implantable sensor; and (d) calculating a radiation dose amount received by the first subject at the target location based on the radiation data obtained from the at least one wireless sensor during and/or after exposure to the first administered dose of radiation to determine and/or verify a dose amount of radiation delivered to the target location.

U.S. Pat. No. 7,361,134 proposes a method of determining the dose rate of a radiation source including locating three or more detectors in the vicinity of a source. Each of the detectors provides an output indicative of the amount of radiation received from the source and determines the location of the source from at least some of the detector outputs. International Pub. No. WO2008148150 proposes a semiconductor radiation sensor.

US20090236510 proposes a radiation dosimeter for measuring a relative dose of a predetermined radiation type within a detection region by using a plurality of scintillating optical fibers. US20060094923 proposes a marker comprising a wireless transponder configured to wirelessly transmit a location signal in response to a wirelessly transmitted excitation energy.

A significant cause of patient discomfort associated with rectal balloons of the prior art is the buildup of gas pressure when the balloon is inserted into the rectum. This buildup of gas pressure can also affect the ability to properly seat the balloon in a desired position. Furthermore, gas buildup is now known to cause a significant amount of prostate movement. Therefore, a device that could eliminate same would be of benefit in allowing margin reductions and thus fewer side effects.

In addition, the rectal balloon is known to move with peristalsis, and movement of the balloon thereby can affect prostate immobilization. Anal clenching will also cause significant movement. Thus, a need exists for a rectal balloon apparatus that is prevented from moving during treatment.

BRIEF SUMMARY OF THE DISCLOSURE

A rectal balloon apparatus comprises a shaft having a fluid passageway extending therethrough. A lumen may be positioned with or be integral to the shaft for movement of rectal gas or other rectal fluids. A flexible tip with one or more openings may be disposed on the end of the shaft and/or the rectal gas relieving lumen inserted into the rectum. The shaft may have a locking device that is slidable longitudinally along the shaft. The locking device may be locked at a desired indicia on the shaft to fix the amount of movement of the shaft into the rectum. In one embodiment, a splitting device disposed with the ends of the shaft and the rectal gas relieving lumen that are not inserted into the rectum may split the lumen from the fluid passageway of the shaft. The lumen port on the splitting device may have a luer lock device for placement of a lumen port cap to prevent the back flow of rectal fluids. A syringe may be positioned with the luer lock to flush the lumen.

A balloon may be affixed over an end of the shaft such that the fluid passageway communicates with an interior of the balloon. The balloon can be converted from a non-inflated condition to an inflated condition. A radiation-detecting sensor may be positioned at any location with the balloon, the shaft, and/or the rectal gas relieving lumen for sensing the amount of radiation delivered. A motion detecting sensor may be positioned at any location with the balloon, the shaft, and/or the rectal gas relieving lumen for sensing the amount of motion or movement of the balloon or surrounding area, such as the part of the rectal wall near the prostate, the shaft, the rectal gas relieving lumen, the radiation sensor, any fiducial markers, and/or any other part of the apparatus. The balloon may have a generally laterally flat surface when in the inflated condition, with a longitudinal groove formed in the laterally flat surface. One or more fiducial markers may be positioned at any location with the balloon, the shaft, and/or the rectal gas relieving lumen. A fiducial marker may be positioned with the flexible tip at the end of the shaft and/or lumen inserted into the rectum. Other types of sensors may be positioned with the balloon, the shaft and/or the lumen. A processor may be used to interpret the information from the different sensors and fiducial markers.

The invention includes one or more of the following embodiments in any and all possible combination(s) thereof:

A locking stopper for a rectal balloon, the stopper having a hemispherical head portion with smoothly rounded surface adjacent the anus, and either a radially central hole or slit therethrough, such that the stopper can be positioned over a balloon shaft or lumen. A base portion of the stopper adjacent the head portion is connected to the head portion and has a hinge that snap closes, squeezing the device slightly over the balloon shaft, thus locking it into position during use. This is very different from other stoppers used on various medical tubing, because the hemispherical distal surface of the stopper is sized and shaped for a comfort fit against the anus, the size (1-2 inches in diameter) preventing further movement and the smoothly rounded surface providing comfort. As used herein, "hemisphere" means half of a sphere (e.g. a half an orange or egg), but perfect sphericity is not required, only that the surface be sufficiently rounded for comfort to delicate tissues.

A prostate immobilizing balloon, said balloon comprising: an inflatable balloon having a proximal end and a distal end; said balloon further comprising a depressed central seating area when fully inflated, wherein said central seating area retains the prostate in a seated position in said central seating area when said balloon is fully inflated and in use in a rectum of a patient; a first lumen communicating with an interior of said balloon, said first lumen having a closable valve; a locking member around said first lumen, said locking member being movable between a locked position and an unlocked position, said locking member having an inner surface suitable for gripping said first lumen when said locking member is in said locked position; a second lumen extending from past said proximal end of said balloon to past said distal end of said balloon, said second lumen having a closed distal tip and one or more ports adjacent said closed distal tip and distal to said balloon; and one or more fiducial markers on a surface thereof.

A locking device for use on a shaft of a prostate immobilizer comprising: a positioning member having a head portion and a stem portion, said stem portion extending from said head portion, said head portion and said stem portion having a channel formed therein, said channel suitable for receiving the shaft therein; and a locking member connected to said stem portion, said locking member being movable between a locked position and an unlocked position, said locking member having a surface suitable for gripping the shaft when said locking member is in said locked position; said head portion having a generally hemispherical shape at one end thereof and a generally flat surface at the opposite end thereof, and said locking member positioned adjacent to said generally flat surface.

Any locking device herein described, said locking member being hingedly connected to said stem portion.

Any locking device herein described, said stem portion having a lip formed thereon, said locking member having a latch formed thereon, said latch engaging said lip when said locking member is in said locked position.

Any locking device herein described, said stem portion having an outer surface flush with a surface of said head portion, said locking member having an outer surface flush with another surface of said head portion when in said locked position.

Any locking device herein described, said head portion having a longitudinal split formed therein so as to open to said channel, said longitudinal split having an opening suitable for allowing the shaft to pass therethrough and into said channel.

A locking device for use on a shaft of a prostate immobilizer comprising: a positioning member having a head portion and a stem portion, said stem portion extending from said head portion, said head portion and said stem portion having a channel formed therein, said channel suitable for receiving the shaft therein; a locking member connected to said stem portion, said locking member being movable between a locked position and an unlocked position, said locking member having a surface suitable for gripping the shaft when said locking member is in said locked position; said head portion having a generally hemispherical shape at one end thereof and a generally flat surface at the opposite end thereof, and said locking member positioned adjacent to said generally flat surface; said stem portion having a lip formed thereon, said locking member having a latch formed thereon, said latch engaging said lip when said locking member is in said locked position; said stem portion having an outer surface flush with a surface of said head portion, said locking member having an outer surface flush with another surface of said head portion when in said locked position.

A prostate immobilizing device, said device comprising: an inflatable balloon having a proximal end and a distal end; said balloon further comprising a depressed central seating area when fully inflated, wherein said central seating area retains the prostate in a seated position in said central seating area when said balloon is fully inflated and in use in a rectum of a patient; a first lumen communicating with an interior of said balloon, said first lumen having a closable valve; any locking member herein described around said first lumen.

Any prostate immobilizing device as herein described, a second lumen extending from past said proximal end of said balloon to past said distal end of said balloon, said second lumen having a closed distal tip and one or more ports adjacent said closed distal tip and distal to said balloon.

Any prostate immobilizing device as herein described, further comprising one or more fiducial markers on a surface thereof, preferably a fiducial marker on a distal tip thereof.

A method of treating prostate cancer by external beam radiation therapy (XRT), comprising: inserting a prostate immobilizing balloon of herein described into a rectum of a patient with a cancerous prostate; inflating said balloon sufficiently to immobilize said prostate in said central seating area; locking said locking member adjacent an anus; and treating said prostate with XRT.

A method of treating prostate cancer by external beam radiation therapy (XRT), comprising: inserting a prostate immobilizing balloon as described into a rectum of a patient with a cancerous prostate; allowing rectal gas to exit the rectum via said one or more ports until no further exiting gas is evident; inflating said balloon sufficiently to immobilize said prostate in said central seating area; locking said locking member adjacent an anus; treating said prostate with XRT; and allowing rectal gas to exit the rectum via said one or more ports during said treating step.

A method of treating prostate cancer by external beam radiation therapy (XRT), comprising: inserting a prostate immobilizing balloon of claim 9 into a rectum of a patient with a cancerous prostate; allowing rectal gas to exit the rectum via said one or more ports until no further exiting gas is evident; inflating said balloon sufficiently to immobilize said prostate in said central seating area; determining the position of said one or more fiducial markers and positioning said balloon such that said fiducial markers are in a desired position; locking said locking member adjacent an anus; treating said prostate with XRT; and allowing rectal gas to exit the rectum via said one or more ports during said treating step.

A prostate immobilizing balloon, said balloon comprising: an inflatable balloon having a proximal end and a distal end; said balloon being sized and shaped for use in a rectum (about 100-120 cc, and about 1-1.5×3-4 inches); a first lumen communicating with an interior of said balloon, said first lumen having a closable valve; the locking member as described around said first lumen.

A method of treating prostate cancer by external beam radiation therapy (XRT), comprising: inserting the prostate immobilizing balloon of claim 14 into a rectum of a patient with a cancerous prostate; inflating said balloon sufficiently to immobilize said prostate; locking said locking member adjacent an anus; and treating said prostate with XRT.

Any prostate immobilizing balloon, said locking member having a hemispherical distal surface for comfortably positioning adjacent an anus when in use.

A method of treating prostate cancer by external beam radiation therapy (XRT), comprising: inserting a prostate immobilizing balloon as herein described into a rectum of a patient with a cancerous prostate; allowing rectal gas to exit the rectum via said one or more ports until no further exiting gas is evident; inflating said balloon sufficiently to immobilize said prostate in said central seating area; determining the position of said one or more fiducial markers and positioning said balloon such that said fiducial markers are in a desired position; locking said locking member adjacent an anus; treating said prostate with XRT; and allowing rectal gas to exit the rectum via said one or more ports during said treating step.

BRIEF DESCRIPTION OF THE DRAWINGS

A better understanding of the present disclosure can be obtained with the following detailed descriptions of the various disclosed embodiments in the drawings:

FIG. 1 is a side elevational view showing a rectal balloon apparatus in an uninflated condition.

FIG. 2 is a side elevational view of a rectal balloon apparatus in an inflated condition.

FIG. 3 is an isolated view showing the compact folding of the balloon over the end of the shaft.

FIG. 4 is a top view of an inflated balloon showing the application of fiducial markers, radiation detecting sensors, and motion detecting sensors.

FIG. 5 is a side view, partially transparent, of a balloon in a first inflated condition.

FIG. 9 is side view of the balloon of the rectal balloon apparatus in an inflated condition.

FIG. 10 is side view, partially transparent, of a balloon in the inflated condition with a rectal gas relieving lumen integral with a shaft, and radiation detecting sensors and motion detecting sensors positioned with the balloon.

FIG. 15 perspective of a gas release balloon cut about half way showing exterior lumen having holes along its length, thus allowing the release of gas trapped along the balloon.

DETAILED DESCRIPTION

Figure 6:
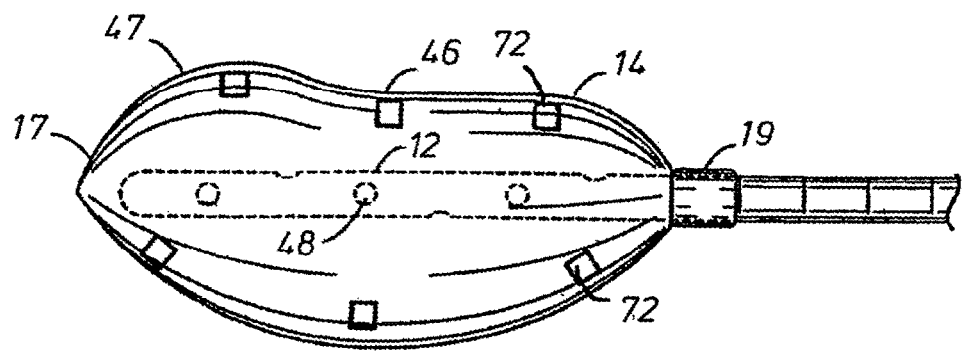
FIG. 6 is a side view, partially transparent, of a balloon in a second inflated condition.

FIG. 1 shows a rectal balloon apparatus 10 comprising a shaft 12 having a fluid passageway extending therethrough. A balloon 14 is affixed over the end 16 of the shaft 12. The balloon 14 is shown in an uninflated or deflated condition. The fluid passageway of the shaft 12 can communicate with the interior of the balloon 14. Also shown is the locking device 13, which is shown in more detail in FIGS. 7 and 7A and discussed below in detail therewith. The locking device 13 serves to assure reproducibility in the positioning of the balloon 14 during radiation therapy.

The shaft 12 may be a generally longitudinal shaft, which has the fluid passageway extending through the center thereof. As used herein, fluid may mean gas, such as air, or liquid, such as water or saline. The shaft 12 is preferably made of a flexible material. A valve assembly 22 may be affixed to the shaft 12 opposite the balloon 14. The valve assembly 22 can have a variety of configurations. FIG. 1 illustrates the valve assembly 22 as an inline valve assembly configuration. The valve assembly 22 may also be an angled valve assembly configuration. The valve assembly 22 includes a stopcock 26. A valve 28 facilitates the ability of the stopcock 26 to open and close so as to selectively allow the fluid to pass into the shaft 12. A port 30 allows the valve assembly 22 to be connected to a supply of the fluid. When the stopcock 26 is opened by the rotation of the valve 28, the fluid will flow through the valve assembly 22, through the interior passageway of the shaft 12 and into the interior of the balloon 14. The valve 28 can then be closed so as to maintain the inflated configuration of the balloon 14. When the procedure is finished and the fluid needs to be removed from the balloon 14, the valve 28 of stopcock 26 can then be opened so as to allow for the release of fluid therethrough.

The opposite end 16 of the shaft 12 may contact the end 32 of the balloon 14. The end 16 may be suitably curved (rounded or dome-shaped) so as to allow the shaft 12 to facilitate the introduction of the balloon 14 into the rectal cavity. The shaft 12 may have indicia 34 formed therealong. It can be seen that the indicia 34 has numerical references associated therewith. These numerical references are indicative of the distance that the balloon 14 has been inserted into the rectum. As such, the indicia 34 provide a clear indication to the medical personnel of the desired location of the rectal balloon 14. An anal dilator ring 19 is shown adjacent an end of the balloon 14.

FIG. 2 illustrates an isolated view of the apparatus 10 after being installed within the rectum. The fluid can be introduced through the valve assembly 22 and through the interior passageway of the shaft 12 so as to inflate the balloon 14. The balloon 14 may have a seating area 15 so that the prostate can be properly positioned thereon. When the balloon 14 is installed and inflated (~100 cc), the prostate may reside on the flat surface 15 in a seated position. After the procedure has been completed, the balloon 14 can be deflated and easily pulled outwardly of the rectum in its deflated condition. In FIG. 2, it can be seen that the locking device 13 has been moved along the shaft 12 (from its position in FIG. 1) to indicia 34, specifically at the number "20." This serves to assure that the balloon 14 will be in a proper position during subsequent radiation treatments.

FIG. 3 shows that the balloon 14 is neatly folded and compressed over the outer diameter of the shaft 12. The shaft 12 may have a rounded end abutting the end 32 of the balloon 14. As such, a comfortable rounded profile may be provided at this end 32. The balloon 14 may be pre-vacuumed during production to produce a minimal profile during use. The anal dilator ring 19 is placed over the shaft 12.

FIG. 4 is a top view of the balloon 14 showing the area of the balloon 14 that preferably engages with the prostate. Central seating area 46 for the prostate is shown as having a groove 52 formed thereon. The groove 52 may be generally rectangular-shaped and may engage with the tip of the prostate, reducing lateral motion. Other configurations of the groove 52 are contemplated. The central seating area 46 and the groove 52 enhance the holding stability of the balloon 14. The head portion 17 of the balloon 14 may be generally tapered. This shape makes insertion of the balloon 14 into the rectum easier for medical personnel and more comfortable for the patient. The balloon 14 may have a thermally welded bond 53 connecting it to the shaft 12. Other forms of bonding are also contemplated.

A first radiation detecting sensor 70 may be located within the groove 52 of the central seating area 46. The sensor 70 allows the treating physician to determine the real time delivery dose of radiation being received at the treatment area when the balloon 14 is in place. The sensor 70 may located in the middle of the groove 52. This location is ideally centrally located on the prostate when the balloon 14 is in place. However, the radiation detecting sensor 70 may be positioned at any other location with the balloon, the shaft, or a rectal gas relieving lumen (not shown). A second radiation detecting sensor 70B is shown disposed with the shaft, and a third radiation detecting sensor 70A is shown positioned with the balloon surface. A radiation detecting sensor may be positioned with any surface of the balloon, the shaft, or a rectal gas relieving lumen. It is also contemplated that a radiation detecting sensor may be positioned unattached in the interior of the balloon.

As shown in FIG. 5, a fourth radiation detecting sensor 70C is positioned on the curved surface 44 of the balloon that is not adjacent the treatment area. Although only one radiation detecting sensor is preferably used, it is contemplated that more than one radiation sensor 70, 70A, 70B, 70C may be used. By positioning the sensor(s) 70, 70A, 70B, 70C near or adjacent to the prostate or other targeted anatomies, an accurate measurement of the radiation delivered to the prostate and/or other targeted anatomies, such as seminal vesicles, may be achieved. The sensors 70, 70A, 70B, 70C can be chosen from any of the available sensors that enable the user to monitor radiation dosage. International Pub No. WO 2008/148150 proposes the preferable type of semiconductor radiation sensor that is contemplated. U.S. Pat. No. 7,361,134 also proposes a type of radiation sensor that is contemplated. It is also contemplated that a radiation sensor using scintillating fiber optics may be used. The sensor 70, 70A, 70B, 70C may be positioned with the balloon, the shaft, or the gas relieving lumen with an adhesive, such as an epoxy glue. However, other attachment means are contemplated as are known in the art.

Six fiducial markers 72 are shown positioned with the balloon 14. Although a plurality of markers 72 are shown, it is contemplated that there may be only one or more fiducial markers 72. It is contemplated that one or more fiducial markers 72A may be positioned anywhere with the balloon, the shaft, or the gas relieving lumen (not shown). A fiducial marker 72A is shown positioned at the very end of the shaft. The fiducial markers 72, 72A may be made of a tungsten material, which may be detected by an MRI or CT scan. Other materials that may be visible on an MRI or CT scan are also contemplated, such as barium sulfate. Fiducial markers in powder or liquid form are contemplated. Through the use of these fiducial markers 72, 72A on the balloon 14 or shaft 12, a treating physician may get a clear image of the position of anterior and posterior walls of the rectum, and/or the position of the rectum relative to the prostate. Fiducial markers 72 may be positioned in spaced relation to each other with the top surface of the balloon 14. For illustrative purposes, three of the fiducial markers 72 are positioned in linear alignment on one side of the groove 52. Another three fiducial markers 72 are arranged on the opposite side of the groove 52. Other combinations and locations of markers 72, 72A are contemplated. A further benefit can be realized by utilizing an additional fiducial marker in the form of a gold seed marker implanted into the prostate. The gold seed marker combined with the fiducial markers 72 allows for triangulation to make certain that the balloon, rectum, and prostate are in the correct positions for treatment.

A first motion detecting sensor 73 is shown within the groove 52 of the central seating area 46. The motion detecting sensor 73 allows the treating physician to determine the movement of any of the radiation sensors 70, 70A, 70B, 70C, fiducial markers 72, 72A, the shaft, the gas relieving lumen, the balloon surface and the surrounding area, such as the part of the rectal wall near the prostate, and/or any other part of the apparatus. Although the motion detecting sensor 73 is shown in the groove 52, one or more motion detecting sensors 73 may be positioned at any other location with the balloon, the shaft, or the gas relieving lumen (not shown). A second motion detecting sensor 73A is shown placed at a different location with the surface the balloon. As shown in FIG. 5, a third motion detecting sensor 73B may be positioned with the curved surface of the balloon that is not adjacent the treatment area. Although only one motion detecting sensor is preferably used, it is contemplated that more than one motion detecting sensor 73, 73A, 73B may be used. The motion detecting sensors 73, 73A, 73B may be selected from any of the available sensors that enable the user to detect motion. It is contemplated that disposable sensors may be used. It is also contemplated that an electromagnetic type motion detecting sensor may be used. Other types of sensors are contemplated.

FIG. 5 is an isolated view of the balloon 14 as inflated to a first inflated condition. In this condition, the balloon 14 has a central seating portion 46, a head portion 17 and a posterior portion 44. When inflated, the central seating area 46 has a lateral flatness for the prostate to rest upon. The lateral flatness of the seating area 46 will prevent the prostate from sliding to one side or the other, and not deform the prostate. The bottom portion 44 is rounded and contacts the rectal wall. The head portion 17 is generally tapered so as to facilitate easier insertion of the balloon 14. The material of the balloon 14 may be formed of a non-latex material, such as medical grade polyurethane, so as to avoid allergic reactions. The shaft 12 is shown extending into the interior of the balloon 14. A plurality of holes 48 may be formed in the shaft 12 through which the balloon 14 is filled with air or other fluid.

For all embodiments shown in all Figures, the balloons, such as balloon 14 in FIG. 5, may have a posterior or bottom portion, such as bottom portion 44, that is made from a different thickness film material than the seating portion, such as seating portion 46. By way of example, the posterior (bottom) portion 44 may be made with a thicker material than the seating (top) portion 46. The thicker material may allow a support structure for the balloon 14, and the thinner material may allow for the seating portion 46 to maintain its shape or have a distal bulge, such as bulge 47 shown in FIG. 6. It is also contemplated that the posterior portion 44 may be thinner than the seating portion 46. The balloon may be made from two or more materials with different thicknesses attached together, such as by thermally welded bond. It is also contemplated that the balloon may be made from two or more materials with the same thickness but with different elasticity properties, such as different modulus of elasticity.

It can be seem that each of the holes 48 is spaced from and offset by 90° from an adjacent hole around the diameter of shaft 12. Other arrangements and orientations are contemplated. A total of six holes may preferably be formed in the shaft 12 within balloon 14 so as to allow the fluid to pass from an interior of shaft 12 to the interior of the balloon 14. Other numbers of holes are contemplated. This arrangement of holes 48 facilitates complete extraction of the fluid from the balloon 14. Under certain circumstances, one of the holes may become clogged or blocked by contact between the body and the balloon, and the staged arrangement assures that the unblocked holes 48 allow the fluid to continues to be easily extracted. In FIG. 5, it can be seen that additional fiducial markers 72 are positioned on the opposite side of balloon 14.

FIG. 6 is an isolated view of the balloon 14 as inflated to a second, more inflated condition (~120 cc). In the second inflated condition, the balloon 14 has a first bulge 47 formed at the head portion 17. The balloon also has a laterally flat seating portion 46. The distal bulge 47 can be utilized in certain conditions to better isolate the prostate and stabilize the seminal vesicles.

Figure 7A:
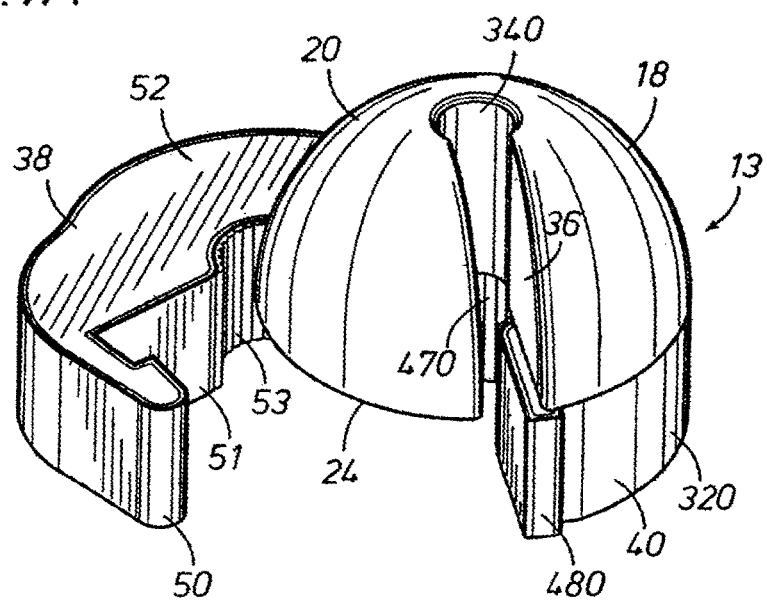
FIG. 7A is a perspective isolated view of the locking device in the unlocked position.
Figure 7:
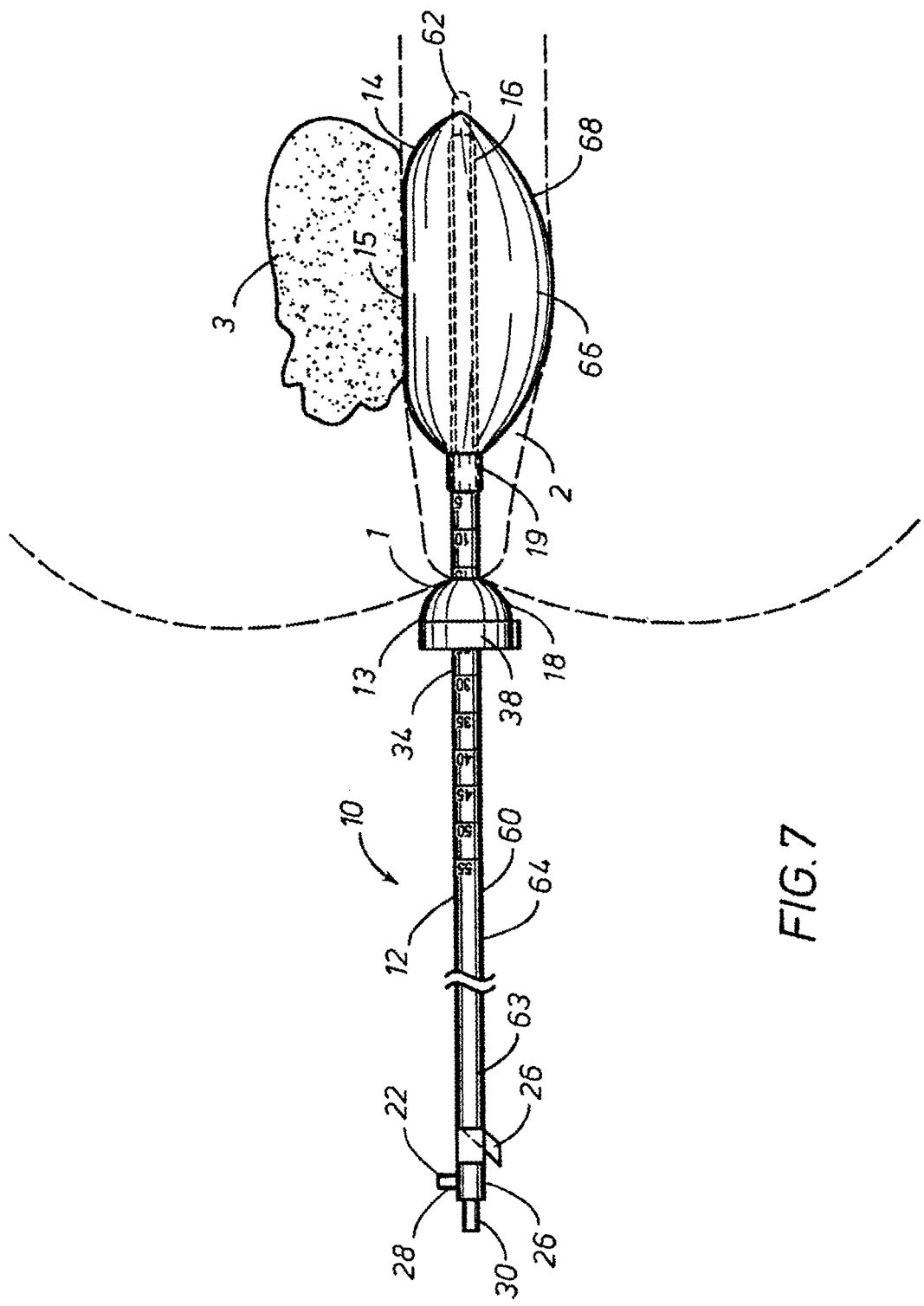
FIG. 7 is a side view of a locking device in the locked position with the rectal balloon apparatus positioned within the anal canal.

Turning to FIG. 7, the prostate immobilizer 10 has a shaft 12 having a fluid passageway 64 extending therethrough, a balloon 14 extending over an end 16 of the shaft 12 such that the fluid passageway 64 communicates with an interior 66 of the balloon 14, a rectal gas relieving lumen 60 extending within the shaft 12 so as have an end 62 opening adjacent an end 68 of the balloon 14, and a locking device 13 for locking a position of the shaft 12 of the prostate immobilizer 10. The device 13 is adjustably slidable along the shaft 12. The device 13 serves to assure uniformity in the positioning of the balloon 14 in the rectal cavity 2 adjacent the prostate 3 during radiation therapy.

The end 16 of the shaft 12 is adjacent the end 68 of the balloon 14. The end 16 of the shaft 12 is suitably rounded so as to allow the shaft 12 to facilitate the introduction of the balloon 14 into the rectal cavity 2. The prostate immobilizer 10 is inserted into the rectal cavity 2 through anus 1. The shaft indicia 34 has numerical references associated therewith. The numerical references are indicative of the distance that the balloon 14 is inserted into the anus 1. The indicia 34 provide a clear indication to medical personnel of the position of the balloon 14 in the rectal cavity 2 for repeatability for subsequent treatments. The balloon 14 can be removed and re-inserted into the rectal cavity 2. The locking device 13 is affixed to the shaft 12 so that the balloon 14 will be repositioned for a same distance into the rectal cavity 2 adjacent the prostate 3.

The locking device 13 is shown as positioned where indicia 34 number "25". The anal dilator ring 19 is affixed to the shaft 12 adjacent the balloon 14. The anal dilator ring 19 may displace the anal verge so as to displace the anal tissue and delineate the anatomy. The anal dilator ring 19 has a diameter greater than a diameter of the shaft 12.

Once the balloon 14 is positioned in a desired location adjacent the prostate 3, medical personnel position the locking device 13 so that it is adjacent the anus 1 and holds the prostate immobilizer 10 in position. The balloon 14 is shown in an inflated condition. The seating area 15 is positioned adjacent the prostate 3 when in the rectal cavity 2. The prostate immobilizer 10 is inserted and removed from the anus 1 in the deflated condition. The lateral flatness of the seating area 15 resists and inhibits the prostate 3 motion. The rounded outer surface of the balloon 14 generally contacts the wall of the rectal cavity 2. The balloon 14 can be formed of a non-latex material, such as polyurethane, so as to avoid allergic reactions.

The gas relieving lumen 60, although shown on the interior of the shaft 12, can be in any other orientation, such as on the outer surface of the shaft 12, that allows for the removal of rectal gas, but preferably is integral with or immediately adjacent the fluid filling shaft. End 62 of the lumen 60 has one or more openings that allow for rectal gas or other bodily fluids to escape from the rectal cavity 2 and out of the lumen 60. A one-way valve can be included along the length of the lumen 60 so as to only allow rectal gas or other bodily fluids to pass from the rectal cavity 2 to the outside environment through the gas relieving lumen 60. The interior of the shaft 12 may be in fluid communication with the interior 66 of the balloon 14 so as to allow fluids to pass into and out of the interior 66 of the balloon 14 for inflation and deflation.

During subsequent radiation treatments, the locking device 13 can be affixed to the shaft 12 in the same position as shown in FIG. 7. As such, when the balloon 14 is inserted, the shaft 12 can be urged forward until the locking device 13 contacts the entrance of the anus. The medical personnel may thus be confident that the balloon 14 is in the proper position. This is accomplished accurately regardless of any change of medical personnel, any squeezing of the sphincter muscles by the patient, and any variations in the amount of lubrication jelly that is used. Repeatability is typically assured. Reproducibility is particularly important when a radiation sensor is used in conjunction with the balloon. It is desirable that the radiation detecting sensor be in the substantially same location each time that it is detecting radiation. When the locking device is affixed to the shaft, it will not be easily displaced. The smooth contour of the outer surface contacting the anus provides comfort to the patient.

In FIG. 7A, the locking device 13 is in an unlocked position prior to attaching to the shaft 12 (not shown). The device 13 has a positioning member 18 and a locking member 38. The positioning member 18 has a head portion 20 and a stem portion 320. The stem portion 320 is integrally formed adjacent an end 24 of the head portion 20. The positioning member 18 has a channel 340 formed therein. The channel 340 extends through each of the head portion 20 and the stem portion 320. The positioning member 18 has a longitudinal split 36 formed therein. The longitudinal split 36 extends through the head portion 20. The longitudinal split 36 communicates with the channel 340. The locking member 38 has a locked position and an unlocked position.

The locking member 38 is hingedly connected to the stem portion 320 of the positioning member 18. The head portion 20 of the positioning member 18 has a hemispherical shape. The stem portion 320 of the positioning member 18 has an outer surface flush with an outer surface of the head portion 20. The longitudinal split 36 extends for the entire length of the head portion 20. The longitudinal split 36 has a width slightly greater than the diameter of the shaft 12. This allows the shaft 12 to be introduced into the channel 340. The channel 340 is sized so as to friction fit the shaft, or the channel can have protrusions to fit the shaft such that closing the device locks it in place.

The stem portion 320 has an outer surface 40 that is flush with an outer surface of the head portion 20. As such, the locking device 13 has smooth contours on the outer surface thereof. The stem portion 320 has a lip 480 extending and angling upwardly and outwardly of the outer surface 40. The lip 480 is generally adjacent to the wall of the longitudinal split 36 of the head portion 20. A curved surface 470 is formed on the interior of the stem portion 320 and has a plurality of ribs formed thereon. The curved surface 470 devices a portion of the channel 340. The longitudinally-extending ribs on the curved surface 470 of channel 340 provide a structure that can suitably grip the outer surface of the shaft so as to facilitate the ability to fix the position of the locking device 13 on shaft 12. Alternatively, the interior can be smooth but made of a tacky material that grips the shaft and/or lumen.

The locking member 38 is hingedly connected to the stem portion 320. The locking member 50 includes a latch 50 that has an edge that will engage the lip 480 of the stem portion 320. The inner surface 51 of the locking member 50 includes a curved area 53. Curved area 53 has ribs to grip and generally corresponds with the location of the curved surface 470 of stem portion 320. As such, curved area 53 will cooperate with the curved surface 470 so as to define the channel 340 of the positioning member 18 when the locking member 38 is in a locked position. The locking member 38 also has an inner surface 52 which will reside in proximity with the end 24 of the head portion 20.

Figure 8:
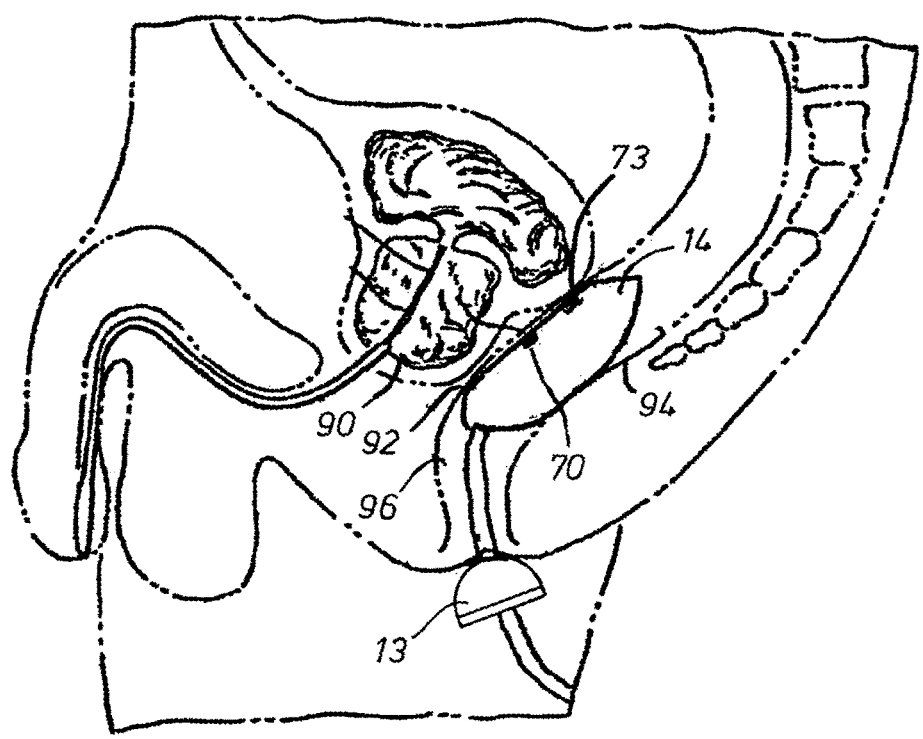
FIG. 8 is side view of the balloon of the rectal balloon apparatus positioned within the rectum and in an inflated condition.

FIG. 8 shows an anatomical side view of the rectal balloon apparatus 10 positioned within a patient's rectum, as it would be during use. The balloon 14 is shown in an inflated condition and positioned up against and between the anterior wall 92 and the posterior wall 94 of the rectum 96. It can be seen that the balloon 14 is positioned adjacent the prostate 90, and that the balloon has been inflated enough to expand the rectum significantly. The fully inflated balloon thus compresses the prostate, tending to immobilize it in position adjacent the inflated balloon, and this reduction in motion allows the treating physician to reduce the treatment margins, thus irradiating less healthy tissue. Further, we now have clinical evidence, that the gas releasing lumen, which allows gas to escape during treatment, even further reduces the mobility of the prostate over a similar balloon lacking the gas release feature, allowing a further reduction in treatment margins.

Additionally, it can be seen that a radiation detecting sensor 70 and a motion detecting sensor 73 are generally positioned adjacent the anterior wall 92 of the rectum 96. It is also contemplated that a plurality of fiducial markers may also be positioned adjacent the anterior wall and/or the posterior wall 94 of the rectum 96, and the balloon position adjusted as needed to ensure reproducible positioning as determined by visualizing the location of the fiducial markers. Thus, when a treating physician can determine the position of the plurality of fiducial markers he or she may obtain a clear image of the contours of the anterior wall 92 and the posterior wall 94 of the rectum 96 by essentially "connecting the dots." The radiation sensor 70 may be used to detect the amount of radiation being received by the target areas, such as the rectal-prostate interface. The motion detecting sensor 73 may detect the movement of any of the sensors, markers, balloon surface or surrounding area, balloon shaft, or other part of the apparatus, allowing the balloon to be repositioned if needed. FIG. 8 also shows the importance of the flexible aspect of the shaft 12 (which allows the technician to move the shaft as needed for filling etc. without inadvertently changing the position of the balloon) and the utilization of the locking device 13. The locking device 13 and numerical indicia provides an initial indication of the depth of positioning of the balloon 14. Thus, the device can be inserted to the same depth with every treatment, and then locked in place against further ingress. The lateral flatness of the balloon 14 is thereby assuredly positioned adjacent the prostate.

The radiation detecting sensor 70 is thereby attempted to be positioned at the same location during all treatments. The sensor 70 can then be used to determine the amount of radiation delivered during each treatment, both daily radiation doses and accumulative radiation for the course of treatment. Treatment is of course halted when the proper radiation level or dosage has been reached.

FIG. 9 is a side view of a rectal balloon apparatus 110 having a balloon 114 with a rectal gas relieving lumen 116 positioned with a surface of the shaft 112. The gas release lumen 116 extends to an exterior of the balloon 114. First opening 118 allows rectal gas or other fluids to pass from an exterior of the balloon 114 into the lumen 116. The rectal gas passes through the lumen 116 to another opening at the opposite end of the lumen 116, and into the atmosphere. The lumen 116 will have a portion extending interior of the balloon 114. The ends of the balloon 114 will be sealed around the lumen 116 and the shaft 112. A flexible lumen tip with ports (or holes), like lumen tip 156 shown in FIG. 12, may be positioned over first opening 118. The flexible lumen tip with ports may provide for patient comfort when the shaft 112 is inserted into the rectum, and also serve to minimize fecal material from entering and clogging or obstructing the gas release lumen 116.

A first radiation detecting sensor 140 may be located with the balloon 114. The sensor 140 is preferably located adjacent the prostate when the balloon 114 is in place. However, the radiation detecting sensor 140 may be positioned at any other location with the balloon 114, the shaft 112, or the lumen 116, including the flexible lumen tip, such as tip 156 in FIG. 12. A second radiation detecting sensor 140A is shown disposed with the shaft, and a third radiation detecting sensor 140B is shown positioned with the lumen. It is also contemplated that a radiation detecting sensor may be positioned unattached in the interior of the balloon. As shown in FIG. 10, a fourth radiation detecting sensor 140C may be positioned on the surface of the balloon that is not adjacent the treatment area. International Pub No. WO 2008/148150 proposes a type of semiconductor radiation sensor that is contemplated. U.S. Pat. No. 7,361,134 also proposes a type of radiation sensor that is contemplated. It is also contemplated that a radiation sensor using scintillating fiber optics may be used. Although only one radiation detecting sensor is preferably used, it is contemplated that more than one radiation sensor 140, 140A, 140B, 140C may be used.

Six fiducial markers 142 are shown positioned with the balloon 114. Although a plurality of markers 142 are shown, it is contemplated that there may be only one or more fiducial markers 142. It is contemplated that one or more fiducial markers 142 may be positioned anywhere with the balloon 114, the shaft 112, or the lumen 116, including a lumen tip with ports. A fiducial marker 142A is shown positioned at the end of the shaft 112. The fiducial markers 142, 142A may be made of a tungsten material, which may be detected by an MRI or CT scan. Other materials that may be visible on an MRI or CT scan are also contemplated, such as barium sulfate. Fiducial markers in powder or liquid form are contemplated. Other combinations and locations of markers 142, 142A are contemplated.

A first motion detecting sensor 143 is shown positioned with the balloon 114. The motion detecting sensor 143 allows the treating physician to determine the movement of the any of the radiation detecting sensors 140, 140A, 140B, 140C, fiducial markers 142, 142A, balloon shaft 112, lumen 116, or the balloon 114 and the surrounding area, such as the part of the rectal wall near the prostate. One or more motion detecting sensors 143 may be positioned at any location with the balloon, the shaft, or the lumen. A second motion detecting sensor 143A is shown placed at a different location with the surface the balloon. The motion detecting sensors 143, 143A may be selected from any of the available sensors that enable the user to detect motion.

FIG. 10 is a side view of a rectal balloon apparatus 120 having a balloon 124 with the gas pressure relieving activity of the rectal gas release lumen 126 integrated with the shaft 122. The shaft 122 extends to an exterior of the balloon 124, and has an opening 128 outside of the balloon 124. A one-way valve means 130 may be formed within the shaft 122. The one-way valve means 130 allows rectal gas to pass from the exterior of the balloon 124, into the opening 128, and through the one-way valve means 130 into the shaft 122. The one-way valve means 130 prevents fluid or rectal gas from escaping through opening 128 from the interior of the shaft 122 when closed, but when open, the one-way valve means 130 operates to allow bodily gas to escape through the interior of the shaft 122 when the balloon 124 is installed in the rectum. Air or other fluid may be introduced into the balloon 124 so as to inflate the balloon 124, while at the same time, closing the one-way valve means 130, thus introducing fluid only to the balloon and not to the patient, and thereafter opened again. It is also contemplated that there may be no one-way valve means, and gas freely escapes via a completely separate air passageway throughout the treatment period. A flexible lumen tip with ports, like tip 156 in FIG. 12, may be positioned over opening 128. The tip shown is closed, and the ports are adjacent thereto, but still distal to the balloon structure. The flexible tip or cap with ports may provide for patient comfort when the shaft 122 is inserted into the rectum, and the closed tip prevents or minimizes bodily material from entering the shaft 122. Radiation detecting sensors 140, 140A, 140B, 140C, fiducial markers 142, 142A, and motion detecting sensors 143, 143A may be positioned with the shaft 122 and/or the balloon 124 of FIG. 10 as shown in FIG. 9. A sensor and/or fiducial marker may be positioned with a flexible tip with ports positioned over first opening 118 of lumen 116.

Figure 11:
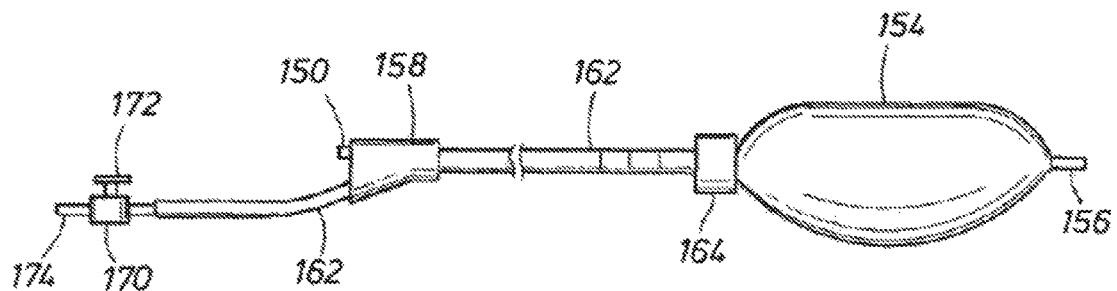
FIG. 11 is side view of a balloon in the inflated condition with a rectal gas relieving lumen inside the fluid passageway of a shaft, a splitting device, and a lumen port cap positioned with the lumen port of the splitting device.

FIG. 11 shows a balloon 154 positioned with shaft 162 having a fluid passageway for inflating and deflating the balloon 154, and the lumen 152 (best shown in FIG. 12) for allowing gas pressure to escape from beyond the end of the balloon. The shaft 162 has ports in the area of the balloon for inflation and deflation, such as previously described. A flexible tip or closed cap 156 is positioned on the end of the lumen 152. Rectal gas may enter the port 168 adjacent the cap 156, and flow through the lumen 152, escaping through the lumen port 150 on the splitting device 158. One or more lumen tip ports 168 are contemplated. As shown in greater detail in FIG. 13, the splitting means 158 splits the lumen 152 from the fluid passageway of the shaft 162. Returning to FIG. 11, anal dilator or collar 164 may be constructed of a hard material and locked over the shaft 162. The collar 164 may have a hinge and a locking mechanism. Valve assembly 170 includes a control knob 172. Turning the control knob 172 serves to close the valve assembly 170 so as to selectively allow the fluid to pass into the shaft 162. A port 174 allows the valve assembly to be connected to a supply of the fluid.

Figure 12:
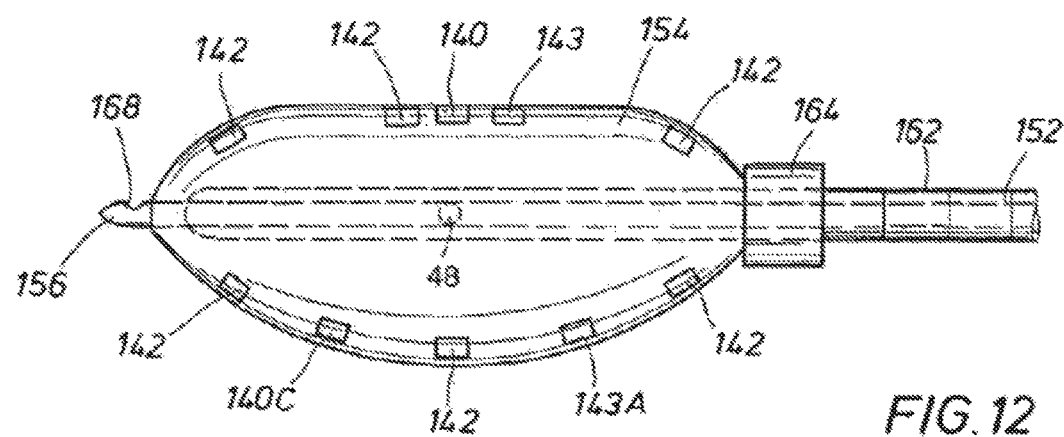
FIG. 12 is an enlarged view of the balloon of FIG. 11.

Turning to FIG. 12, radiation detecting sensors 140, 140A, 140B, 140C, fiducial markers 142, 142A, and motion detecting sensors 143, 143A may be positioned with the shaft 162 and/or the balloon 154 similarly as shown in FIG. 9. A sensor and/or fiducial marker may be positioned with flexible lumen tip 156.

Figure 13:
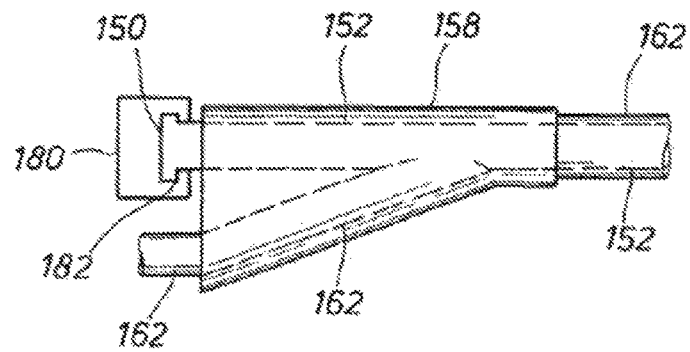
FIG. 13 is an enlarged view of the splitting device of FIG. 11 showing the lumen port cap disposed with a luer lock.

In FIG. 13, the lumen port 150 on the splitting device 158 may have a lip formation 182 for placement of a lumen port cap 180. A luer lock formation or device is contemplated. It is contemplated that the cap 180 may be threadingly attached with the lumen port 150. Other attachment means as are known in the art are contemplated. The cap advantageously prevents fluid from escaping the lumen 152.

Figure 14A:
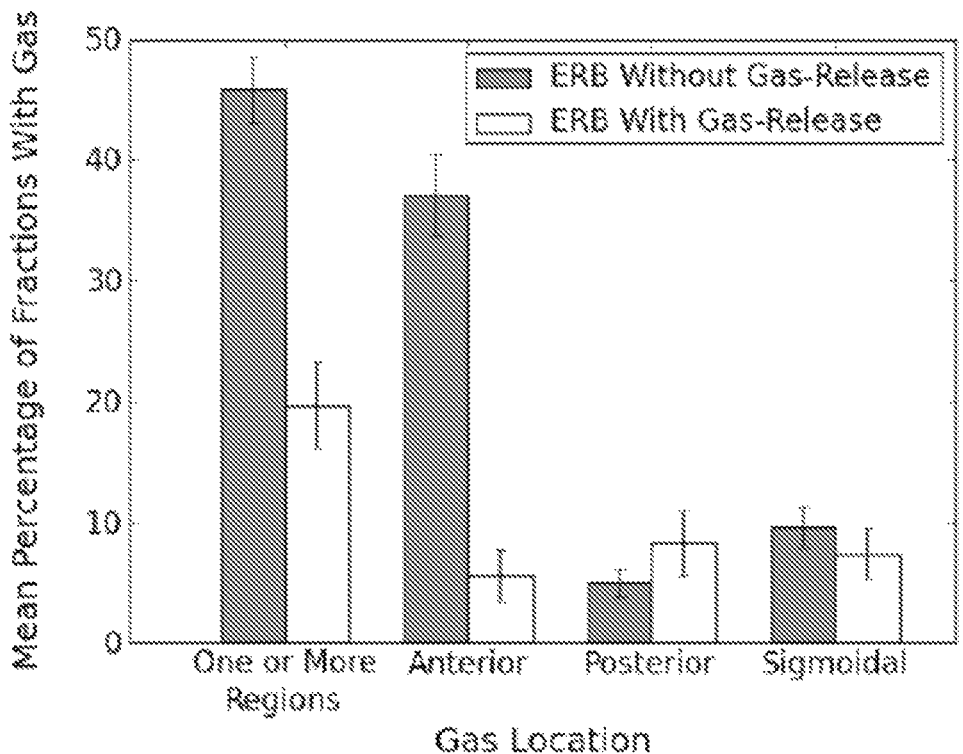
FIG. 14A Mean frequency of rectal gas according to region and type of ERB used. The mean incidences of gas in one or more regions and in the anterior region differed at statistically significant levels ($p<0.00001$ and $p<0.0000001$, respectively) between the standard and gas-release ERBs. Error bars represent the standard deviation of the mean of within patient means.
Figure 14B:
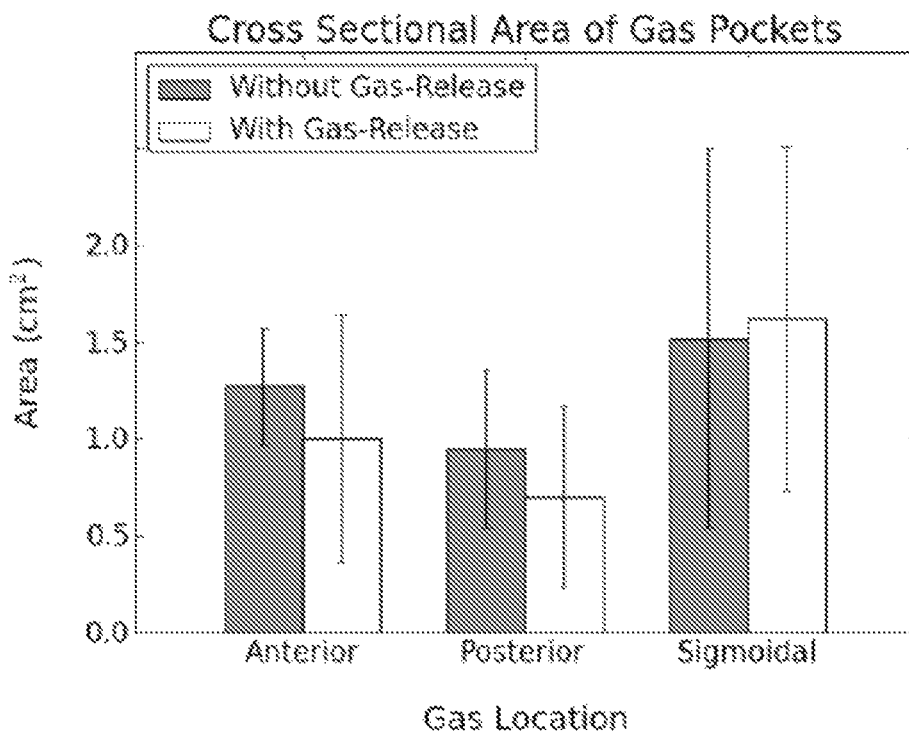
FIG. 14B size of gas pockets. From Wooton 2012.

A retrospective study was performed comparing to quantify the effects an ERB with a passive gas release conduit had on the incidence of rectal gas (Wooten 2012). Fifteen patients who were treated with a standard ERB and with a gas-release ERB (both from RadiaDyne) were selected and location and cross-sectional area of gas pockets and the fraction of time they occurred on lateral kilovoltage (kV) images were analyzed. Gas locations were classified as trapped between the ERB and anterior rectal wall, between the ERB and posterior rectal wall, or superior to the ERB, e.g towards the sigmoidal colon. The results, shown in FIGS. 14A and B show that the gas-release ERB significantly decreased the number of fractions in which gas was present, primarily by decreasing the incidence of gas trapped between the rectal balloon and the anterior rectal wall. Therefore, the study recommended that gas-release ERBs be used in patients undergoing radiation therapy for prostate cancer.

Another study by Su found that compared to non-gas release balloons, gas release balloon reduced the magnitude of intrafractional prostate motion in both AP and SI directions. Thus, it allowed smaller treatment margins (Su 2012).

The prevalence of gas found in the anterior region is consistent with previous findings and knowing that gas is most likely to be trapped in the anterior region is important because gas trapped there will not only displace the prostate, but also push the anterior rectal wall into the treatment field. This could potentially alter the prostate and rectal dose distribution and possibly the treatment outcome.

In X-ray conformal or intensity-modulated radiation therapy, such a change in dose distribution would likely be small, and the negative effects of gas would stem mostly from organ displacement. However, in proton radiation therapy, gas in the treatment field can escalate dose to normal tissue to an unacceptably high level because of the extreme sensitivity of protons to the medium they travel through. A proton beam's range, and thus energy deposition, is extremely sensitive to the density of the medium through which the beam passes. Gas in the posterior and sigmoid regions can also displace the prostate, but this occurrence was not common when using either model of ERB in our analysis.

The cross-sectional areas of gas pockets did not change significantly with respect to ERB model used demonstrating that, although gas occurs less often with the gas-release balloon, the severity of the gas is not decreased by it. A possible explanation for this result could be hasty gas-release ERB insertion that does not allow time for gas to escape through the conduit before being trapped when the balloon is inflated.

If this is the case, the gas-release ERB could be used to better advantage by slow, careful insertion, giving the gas time to escape during all points of the insertion. Thus, inflation would not begin until the technician was reasonably sure that sufficient time was allowed for all gas to escape. Alternatively, additional gas releasing lumens can be glued to the exterior of the balloon, especially on the anterior side which sits adjacent the prostate, with holes there along to allow anterior gas pockets to escape.

This shown in FIG. 15, a cross sectioned half of a gas release balloon having an exterior mounted gas release lumen. The balloon is made of bottom layer 1501 welded 1503 to top layer 1501 around the edges. If desired, this balloon can be shaped as described above, but such details are omitted from this figure for the sake of clarity. An optional central lumen is bifurcated at this point, providing a gas release passageway 1507, as well as a balloon filling passageway 1509 that allows air to enter the balloon. Exterior gas release lumen 1511 is mounted to the outer layer of the balloon, e.g., by gluing or other welding process, and that lumen 1511 has openings 1513 along its length for allowing the escape of gas pockets trapped alongside the balloon. The posterior of the balloon can also be equipped with a similar lumen 1515, but this is optional, as gas on this side of the balloon may present less of a problem due to the distance from the prostate. Central lumen 1507/1509 is optional in this embodiment, although shown herein, because the exterior lumen can serve the insertion function and can be provided with closed distal tip and ports.

An important advantage of passive gas release over catheterization is that it continues to work during patient treatment. Although existing rectal gas may be removed by a catheter at the beginning of treatment, gas may continue to build up during the course of the treatment, and this occurrence has been documented. The passive gas release balloon described herein alleviates build of gas upstream of the balloon, and if provided with an exterior gas release passageway mounted on an exterior surface of the balloon, even gas trapped alongside the balloon can be assured of release.

The foregoing disclosure and description of the invention are illustrative and explanatory thereof, and various changes in the details of the illustrated apparatus and system, and the construction and method of operation may be made without departing from the spirit of the invention.

The following are incorporated by reference herein in their entireties for all purposes.

Wooten et al., Effectiveness of a novel gas-release endorectal balloon in the removal of rectal gas for prostate proton radiation therapy J. APPL. CLIN. MED. PHYS. 13(5): 190-197 (2012).

Su, et al., Abstract 3192 Reduction of Prostate Intrafraction Motion using Gas-release Rectal Balloons, I. J. Radiation Oncology*Biology*Physics 81(2) (S. 2011).

Su et al., Reduction of prostate intrafraction motion using gas-release rectal balloons, 5869 Med. Phys. 39 (10): 5869 (2012).

U.S. Pat. No. 3,509,884; U.S. Pat. No. 4,813,429; US20030028097; US20060094923; US20070058778; US20090236510; U.S. Pat. No. 5,476,095; U.S. Pat. No. 6,963,771; U.S. Pat. No. 7,361,134; U.S. Pat. No. 8,500,771; WO1994023676

I claim:

1. A locking device for use on a lumen of a prostate immobilizer comprising:
   a) a positioning member having a head portion and a stem portion, said stem portion extending from said head portion, said head portion and said stem portion having a channel formed therein, said channel suitable for receiving a lumen therein; and
   b) a locking member connected to said stem portion, said locking member being movable between a locked position and an unlocked position, said locking member having a surface suitable for gripping the lumen when said locking member is in said locked position;
   wherein said head portion having a generally hemispherical shape at one end thereof and a generally flat surface at the opposite end thereof, and said locking member positioned adjacent to said generally flat surface.

2. The device of claim 1, said locking member being hingedly connected to said stem portion.

3. The device of claim 2, said stem portion having a lip formed thereon, said locking member having a latch formed thereon, said latch engaging said lip when said locking member is in said locked position.

4. The device of claim 1, said stem portion having an outer surface flush with a surface of said head portion, said locking member having an outer surface flush with another surface of said head portion when in said locked position.

5. The device of claim 1, said head portion having a longitudinal split formed therein so as to open to said channel, said longitudinal split having an opening suitable for allowing the lumen to pass therethrough and into said channel.

6. A locking device for use on a lumen of a prostate immobilizer comprising:
   a) a positioning member having a head portion and a stem portion, said stem portion extending from said head portion, said head portion and said stem portion having a channel formed therein, said channel suitable for receiving a lumen therein;
   b) a locking member connected to said stem portion, said locking member being movable between a locked position and an unlocked position;
   c) said locking member having a surface suitable for gripping said lumen when said locking member is in said locked position;
   d) said head portion having a generally hemispherical shape at one end thereof and a generally flat surface at the opposite end thereof, and said locking member positioned adjacent to said generally flat surface;
   e) said stem portion having a lip formed thereon, said locking member having a latch formed thereon, said latch engaging said lip when said locking member is in said locked position;
   f) said stem portion having an outer surface flush with a surface of said head portion, said locking member having an outer surface flush with another surface of said head portion when in said locked position.

7. A prostate immobilizing device, said device comprising:
   i) an inflatable balloon having a proximal end and a distal end;

ii) said balloon being sized and shaped for use in a rectum of an adult human male;
iii) a first lumen communicating with an interior of said balloon, said first lumen having a closable valve;
iv) the locking member of claim 1 around said first lumen such that said first lumen is in said channel.

8. The device claim 7, a second lumen extending from past said proximal end of said balloon to past said distal end of said balloon, said second lumen having a closed distal tip and one or more ports adjacent said closed distal tip and distal to said balloon.

9. The device of claim 8, further comprising one or more fiducial markers on a surface thereof.

10. The device of claim 8, further comprising a fiducial marker on a distal tip thereof.

11. A method of treating prostate cancer by external beam radiation therapy (XRT), comprising:
 a) inserting a prostate immobilizing balloon of claim 7 into a rectum of a patient with a cancerous prostate;
 b) inflating said balloon sufficiently to immobilize said prostate;
 c) locking said locking member adjacent an anus; and
 d) treating said prostate with XRT.

12. A method of treating prostate cancer by external beam radiation therapy (XRT), comprising:
 a) inserting a prostate immobilizing balloon of claim 8 into a rectum of a patient with a cancerous prostate;
 b) allowing rectal gas to exit the rectum via said one or more ports until no further exiting gas is evident;
 c) inflating said balloon sufficiently to immobilize said prostate in said central seating area;
 d) locking said locking member adjacent an anus;
 e) treating said prostate with XRT; and
 f) allowing rectal gas to exit the rectum via said one or more ports during said treating step.

13. A method of treating prostate cancer by external beam radiation therapy (XRT), comprising:
 a) inserting a prostate immobilizing balloon of claim 9 into a rectum of a patient with a cancerous prostate;
 b) allowing rectal gas to exit the rectum via said one or more ports until no further exiting gas is evident;
 c) inflating said balloon sufficiently to immobilize said prostate in said central seating area;
 d) determining the position of said one or more fiducial markers and positioning said balloon such that said fiducial markers are in a desired position;
 e) locking said locking member adjacent an anus;
 f) treating said prostate with XRT; and
 g) allowing rectal gas to exit the rectum via said one or more ports during said treating step.

14. A prostate immobilizing device, said device comprising:
 i) an inflatable balloon having a proximal end and a distal end;
 ii) said balloon being sized and shaped for use in a rectum of an adult human male;
 iii) a first lumen communicating with an interior of said balloon, said first lumen having a closable valve;
 iv) the locking member of claim 6 around said first lumen so that said lumen is in said channel.

15. The device claim 14, a second lumen extending from past said proximal end of said balloon to past said distal end of said balloon, said second lumen having a closed distal tip and one or more ports adjacent said closed distal tip and distal to said balloon.

16. The device of claim 15, further comprising one or more fiducial markers on a surface thereof.

17. The device of claim 15, further comprising a fiducial marker on a distal tip thereof.

18. A method of treating prostate cancer by external beam radiation therapy (XRT), comprising:
 a) inserting a prostate immobilizing balloon of claim 14 into a rectum of a patient with a cancerous prostate;
 b) inflating said balloon sufficiently to immobilize said prostate;
 c) locking said locking member adjacent an anus; and
 d) treating said prostate with XRT.

19. A method of treating prostate cancer by external beam radiation therapy (XRT), comprising:
 a) inserting a prostate immobilizing balloon of claim 15 into a rectum of a patient with a cancerous prostate;
 b) allowing rectal gas to exit the rectum via said one or more ports until no further exiting gas is evident;
 c) inflating said balloon sufficiently to immobilize said prostate in said central seating area;
 d) locking said locking member adjacent an anus;
 e) treating said prostate with XRT; and
 f) allowing rectal gas to exit the rectum via said one or more ports during said treating step.

20. A method of treating prostate cancer by external beam radiation therapy (XRT), comprising:
 a) inserting a prostate immobilizing balloon of claim 16 into a rectum of a patient with a cancerous prostate;
 b) allowing rectal gas to exit the rectum via said one or more ports until no further exiting gas is evident;
 c) inflating said balloon sufficiently to immobilize said prostate in said central seating area;
 d) determining the position of said one or more fiducial markers and positioning said balloon such that said fiducial markers are in a desired position;
 e) locking said locking member adjacent an anus;
 f) treating said prostate with XRT; and
 g) allowing rectal gas to exit the rectum via said one or more ports during said treating step.

* * * * *